United States Patent [19]

Bertini et al.

[11] 4,198,348

[45] Apr. 15, 1980

[54] PROCESS FOR THE PREPARATION OF AMINES

[75] Inventors: Franco Bertini, S. Felice; Carlo A. Pauri, Colleferro, both of Italy

[73] Assignee: SNIA VISCOSA Societa Nazionale Industria Applicazioni Viscosa S.p.A., Milan, Italy

[21] Appl. No.: 913,695

[22] Filed: Jun. 8, 1978

[30] Foreign Application Priority Data

Jun. 14, 1977 [IT] Italy ............................... 24640 A/77

[51] Int. Cl.$^2$ ............................................ C07C 85/147
[52] U.S. Cl. ............................ 260/563 C; 260/563 R; 260/570.8 R; 260/570.9; 260/583 R
[58] Field of Search .................... 260/578; 260/563 C, 260/578, 583 L, 563 R, 570.8 R, 570.9, 583 R

[56] References Cited

U.S. PATENT DOCUMENTS

| 965,903 | 8/1910 | Hofmann et al. ............... 260/583 L |
| 991,721 | 5/1911 | Hofmann et al. ............... 260/583 L |
| 1,489,380 | 4/1924 | Bader et al. ...................... 260/583 L |

OTHER PUBLICATIONS

Wallis et al., "The Hofmann Reaction" in *Organic Reactions*, vol. III, 1946, John Wiley & Sons, Inc., pp. 267–286, 291, 294, 296.

*Primary Examiner*—John Doll
*Attorney, Agent, or Firm*—Wenderoth, Lind & Ponack

[57] ABSTRACT

There is described a process for the preparation of amines of the type $RNH_2$, wherein R represents a hydrocarbon radical containing up to 18 carbon atoms, in particular an aliphatic, arylaliphatic, cycloaliphatic or aromatic radical, the said process being characterized by the fact that an amide having the formula $RCONH_2$, wherein R has the aforesaid meaning, is reacted, at a pH less than or equal to 7, firstly with gaseous chlorine, in the absence or in the presence of a diluent, and the N-chloroamide thus formed is subsequently reacted with an alkali hydroxide and/or an earth alkali hydroxide.

12 Claims, No Drawings

PROCESS FOR THE PREPARATION OF AMINES

BACKGROUND OF THE INVENTION

1. The Field of the Invention

The present invention relates to a new process for the preparation of primary aromatic, cycloaliphatic, aliphatic or arylaliphatic amines.

2. The prior Art

It is known that the amines may be prepared by degradation of the amides of the corresponding acids, containing one carbon atom more than the amine which it is desired to obtain, by treatment with hypochlorite or hypobromite in alkaline medium (Hofmann degradation); said reaction may be represented by the following overall equation (when sodium hydroxide is used as the alkaline hydroxide and chlorine as the halogen):

$$R-CONH_2 + Cl_2 + 4NaOH \rightarrow R-NH_2 + 2NaCl + Na_2CO_3 + 2H_2O$$

wherein R represents an organic radical.

This reaction is practically carried out in the industry in two stages which may be represented by the following equations:

$$2NaOH + Cl_2 \rightarrow NaCl + NaClO + H_2O \quad (a)$$

$$RCONH_2 + NaClO + 2NaOH \rightarrow R-NH_2 + NaCl + Na_2CO_3 + H_2O \quad (b)$$

As it appears from these equations, four mols of sodium hydroxide (or of other alkali hydroxides) are required for each mol of amine obtained. This is because two mols of hydroxide are used up to obtain one mol of hypochlorite, while two more mols are necessary for the Hofmann degradation proper.

The Applicant has now surprisingly found that it is possible to obtain the same result by using a smaller molar ratio of alkali hydroxide employed to amine obtained; this may be achieved by reacting, at a pH less than or equal to 7, the amide ($RCONH_2$) firstly with gaseous chlorine in the presence or absence of a diluent, and subsequently reacting the formed N-monochloroamide with an alkali and/or an earth-alkali hydroxide, such as barium or calcium hydroxide, to obtain the corresponding amine ($RNH_2$) with comparable yields. In the case that sodium hydroxide is used as the alkali hydroxide and calcium hydroxide as the earth-alkali hydroxide, the reactions according to the invention may be represented as follows:

$$RCONH_2 + Cl_2 \rightarrow RCONHCL + HCl \quad (\alpha)$$

$$RCONHCL + 2NaOH \rightarrow RNH_2 + NaHCO_3 + NaCl \quad (\beta)$$

$$2RCONHCL + 3Ca(OH)_2 \rightarrow 2RNH_2 + 2CaCO_3 + CaCl_2 + 2H_2O \quad (\gamma)$$

$$RCONHCL + NaOH + Ca(OH)_2 \rightarrow RNH_2 + NaCl + CaCO_3 + H_2O \quad (\delta)$$

The economic advantage of using, for each mol of amine formed, only two mols of sodium hydroxide or 1½ mols of calcium hydroxide, or a mixture of the two, is obvious, both because a smaller quantity of hydroxides is used, and because calcium hydroxide is considerably cheaper than sodium hydroxide.

The object of the present invention is therefore a process for the preparation of amines of the $RNH_2$ type, wherein R represents a hydrocarbon radical containing up to 18 carbon atoms, in particular an aliphatic, arylaliphatic, cycloaliphatic or aromatic radical, characterized by the fact that an amide having an $RCONH_2$ formula, wherein R has the aforesaid meaning, is reacted, at a pH less than or equal to 7, firstly with gaseous chlorine, in the presence or in the absence of a diluent, and that the N-chloroamide thus formed is subsequently reacted with an alkali hydroxide and/or an earth-alkali hydroxide in particular barium or calcium hydroxide. Preferably the molar ratio of the $(OH)^-$ groups of said hydroxides with respect to the —(CONHCl) group of said amine is practically maintained smaller than or equal to 3:1.

The saving of alkali hydroxide, earth-alkali hydroxide, or the mixture of the two, may practically be as high as 50% with respect to what is required by the classic Hofmann reaction.

The chlorination of the amide $RCONH_2$ is conveniently effected at a temperature comprised between $-20°$ and $+80°$ C., preferably between $+10°$ and $+20°$ C., optionally under pressure.

As a diluent it is possible to use e.g. water, chloroform, carbon tetrachloride, trieline, and all the diluents which do not undergo chlorination in the sunlight in the presence of elementary chlorine; obviously it is possible to effect the chlorination of the amide also in the presence of a mixture of said diluents.

The reaction between the N-chloroamide obtained and the alkali hydroxide and/or the earth-alkali hydroxide, is effected in the presence of a suitable diluent (e.g. water) at a temperature comprised between 0° and 100° C. and preferably between 0° and 80° C.

As an alkali hydroxide, e.g. potassium or preferably sodium hydroxide may be used. Preferably calcium hydroxide is used as an earth-alkali hydroxide. It may be convenient to employ at least a part of an alkali hydroxide in the hydroxylated component. The amine obtained is separated by conventional methods known in the literature with reference to the specific amine formed.

According to the present invention, it may be preferable to separate the N-chloroamide from the reaction mixture before reacting it with the alkali and/or earth-alkali hydroxide/hydroxides. Obviously it is also possible to employ a mixture of hydroxides of several alkali and/or earth-alkali metals.

According to the present invention it is possible to operate either discontinuously or continuously.

By operating according to the present invention, a further advantage is attained: actually the separation of the two reaction stages, according to the present invention, permits to employ the cheaper calcium hydroxide which, while it is indicated as operative in the known art, is practically hardly usable because of the instability of the calcium hypochlorite.

The amines obtained by the process according to the invention form a further object of the present invention.

The following examples are illustrative but do not limit the present invention.

EXAMPLE 1

A stream of gaseous chlorine is introduced at a speed of 60 g/h into a solution of 127 g of hexahydrobenzamide (1 mol) in 600 ml of $CHCl_3$, maintained at 0° C. 78 g of chlorine (1.099 mols), controlled by weighing, are absorbed in 78 min.

The chlorinated product thus formed is poured onto 500 g of ground ice, the chloroform solution is separated and is washed with water until it becomes neutral. A residue of 161 g of N-chlorohexahydrobenzamide (quantitative yield) the active chlorine content of which is 22% (theoretical 21.93%) is obtained by evaporation of the solvent.

64.64 g (0.4 mol) of N-chlorohexahydrobenzamide 100%, obtained as set forth above, is added during an hour to a solution of 32.32 g of 99% pure sodium hydroxide (0.8 mol) dissolved in 400 ml of water and maintained at a temperature comprised between 20° and 22° C.

The mixture thus obtained is kept under stirring for one hour at 20° C., then it is heated for one hour at 80° C., and the cyclohexylamine/water azeotropic mixture thus obtained is distilled (distillation temperature 96° C.; cyclohexylamine content in the azeotropic mixture: 44.4%).

188 g containing 21% by weight of cyclohexylamine are thus obtained, which corresponds to a yield of 99.4% of theory.

EXAMPLE 2

Gaseous chlorine is introduced at a speed of 66 g/h into a suspension of 256 g of hexahydrobenzamide(2 mols) in 1700 ml of water maintained under stirring at 20° C. After 2 h and 28 min 163 g of chlorine have been obsorbed, corresponding to 2.3 mols. After separating the N-chlorohexahydrobenzamide from the suspension by filtration, it is washed with water until the acidity has been eliminated.

310 g of N-chlorohexahydrobenzamide (yield 95.75%) having a chlorine content of 21.1% (theoretical value 21.93%) are thus obtained. 67.18 g (0.4 mol) of 96.22% pure N-chlorohexahydrobenzamide obtained as hereinbefore described, are added during one hour to a suspension of 46.79 g of 95% pure calcium hydroxide (0.6 mol) in 2500 ml of water maintained at a temperature of 20°-25° C.

The mixture is stirred at 20°-25° C. until all active chlorine has disappeared, is heated for another 30 min at 80° C., then the cyclohexylamine is distilled in azeotropic mixture with water at a temperature between 96° and 99° C., whereby 468 g of a solution containing 7.79% of cyclohexylamine, corresponding to a yield of 92% of theory, are obtained.

EXAMPLE 3

33 g of N-chlorohexahydrobenzamide, 98% pure, (0.2 mol) are added slowly under stirring to a suspension of 8.1 g of 98.5% pure NaOH (0.2 mol) and 15.6 g of 95% pure calcium hydroxide (0.2 mol) in 2300 ml of water at the temperature of 20° C. The mixture is stirred for some hours at 20° C. until all active chlorine in the solution has disappeared, then is heated for 30 min at 80° C., and the cyclohexylamine is distilled in the form of an azeotropic mixture with water, whereby 186 g of a solution containing 10% of cyclohexylamine, corresponding to a yield of 93.6% of theory, are obtained.

EXAMPLE 4

33.24 g of 97.17% pure N-chlorohexahydrobenzamide (0.2 mol) are added in 30 min at 20° C. to a mixture of 8.1 g of 98.5% pure NaOH (0.2 mol) and 65 g of 97% pure $Ba(OH)_2.8H_2O$ (0.2 mol) dissolved in 1200 ml of $H_2O$. After another 30 min of stirring at 20° C., the mass is heated at 80° C. for 30 min, and finally the azeotropic mixture water-cyclohexylamine is distilled, a total of 450 g of alkaline waters being collected. The content of cyclohexylamine in the waters is determined and is found to be 4.3%, corresponding to a yield of 97.7%.

EXAMPLE 5

33.2 g of N-chlorohexahydrobenzamide, 97.17% pure, (0.2 mol) is added under stirring in the course of 30 min at 20° C. to a solution of 97 g of 97.5 pure $Ba(OH)_2.8H_2O$ (0.3 mol) in 850 ml of water. The reaction mass is slowly heated to 60° C. and is maintained at said temperature for another 30 min, then the temperature is raised to 80° C. for another 30 min and finally the azeotropic mixture water-cyclohexylamine is distilled. The collected solution, 426 g, contains 4.6% of cyclohexylamine, corresponding to a yield of 98.6%.

EXAMPLE 6

A stream of gaseous chlorine in introduced at a speed of about 33 g/h into a suspension of 111 g of 99.5% pure benzamide (0.91 mol) in 700 ml of water maintained at a temperature of 15°-20° C. After 2 h and 15 min 75 g of chlorine (1.05 mol), controlled by weighing, have been absorbed. The mass is stirred for another 15 min at a temperature of 20° C., then the chlorinated product obtained is filtered off and is washed with water until the hydrochloric acid has disappeared. 140 g of N-chlorobenzamide (yield 98.9%) containing 21.87% of active chlorine, corresponding to a titer of 96%, are obtained.

48.6 g of 96% pure N-chlorobenzamide (0.3 mol) is added at 16°-20° C. under good stirring in the course of 15-20 min to a solution of 24.2 g of 99% pure NaOH (0.6 mol) in 95 ml of water.

After some hours, when there is no more active chlorine in the solution, the mixture is quickly heated to 80° C. and this temperature is maintained for 30 min, whereafter it is cooled and extracted several times with chloroform. 256 ml of a chloroform extract having a gas chromatographic titer of 10.47% in aniline, corresponding to a yield of 95.96% of theory, are collected.

EXAMPLE 7

32.4 g of 96% pure N-chlorobenzamide (0.2 mol) are added at 15°-20° C., under good stirring, in the course of 30-40 min, to an aqueous suspension consisting of 15.6 g of 95% pure $Ca(OH)_2$ (0.2 mol) and 8.1 g of 98.5% pure NaOH (0.2 mol) in 2000 ml of water. The temperature of 20° C. is maintained for 2 hours, thereafter the mass is heated for 1 hour at 40°-50° C. and finally the temperature is quickly brought to 80° C. and is maintained at said level for about 30 min. When the reaction hs been completed the aniline is distilled in a steam stream. 557 g of alkaline waters are distilled, which separate the thick oil characteristic of aniline. For carrying out the analysis, the mass is brought to the volume of 1000 ml with ethyl alcohol and the hydroalcoholic solution of aniline is analized chromatographically. The titer is found to be 1.73% of aniline, corresponding to a yield of 93%.

EXAMPLE 8

A suspension of 26.52 g of 95% pure calcium oxide (0.45 mol) in 1000 ml of water is stirred until all the oxide has been transformed to hydroxide. The suspension is cooled to 15° C. and 49.54 g of 94.2% pure N-chlorobenzamide (0.3 mol) are gradually added under stirring. The reaction temperature is maintained between 20° and 25° C. under stirring until all active chlorine has disappeared from the solution. The reaction is completed by heating rapidly to 80° C. for 30 min, finally the aniline formed is distilled in a steam stream until neutral waters are obtained. 900 ml of a solution of aniline having a chromatographic titer of 2.85%, corresponding to a yield of 91.9%, are thus collected.

EXAMPLE 9

Gaseous chlorine is introduced at a speed of 95 g/h into a suspension of 194 g of 98.15% pure pelargonamide (1.21 mol) in 1400 ml of water. The introduction of chlorine is discontinued after 60 min and the suspension is still left under stirring for 20-30 min at 20° C. The solid is filtered off, is washed with water until all HCl has disappeared (300 cc. of water) and the chlorinated derivative is dried. 226 g of N-chloropelargonamide (yield 97.4%) having an active chlorine titer of 17.6% (theory 18.5%) are thus obtained.

40.3 g of 95.15% N-chloropelargonamide (0.2 mol) are gradually added in the course of 30 min under stirring and at 10°-15° C., to a solution of 16.3 g of 98% pure NaOH (0.4 mol) in 64 ml of $H_2O$. After having maintained the reaction mass at 20° C. for 2 hours, the reaction is completed at 80° C. in the course of 30 min. The amine produced is extracted from the water, in which it is only slightly soluble, with ethyl ether. The extract, 133 g, contains 18.2% of octylamine, corresponding to a yield of 93.7%.

We claim:

1. A process for the preparation of an amine of the formula $RNH_2$, wherein R represents a hydrocarbon radical containing up to 18 carbons selected from the group consisting of an aliphatic radical, an arylaliphatic radical, a cycloaliphatic radical and an aromatic radical, said process comprising reacting an amide having the formula $RCONH_2$, wherein R has the aforesaid meaning at a pH less than or equal to 7 with gaseous chlorine, in a medium free of alkaline or alkaline earth metal hydroxide to form the corresponding N-chloroamide, isolating the thus formed N-chloroamide and subsequently reacting said N-chloroamide with an alkali hydroxide, an earth alkali hydroxide or a mixture thereof, the molar ratio of the $(OH)^-$ groups of said hydroxides to the $(CONH)^-$ group of said amide being maintained at a value smaller than or equal to 3:1.

2. Process according to claim 1, wherein R represents an alkyl, cycloalkyl or phenyl radical.

3. Process according to claim 2, wherein R represents an octyl, cyclohexyl or phenyl radical.

4. Process according to claim 1, wherein the chlorination of the amide $RCONH_2$ is effected at a temperature of between −20° and +80° C.

5. Process according to claim 4, wherein said chlorination is effected at a temperature of between +10° and +20° C.

6. Process according to claim 1, wherein the chlorination of the amide $RCONH_2$ is effected under pressure.

7. Process according to claim 1 wherein the reaction of the amide with chlorine is carried out in a diluent selected from the group consisting of water, chloroform, carbontetrachloride, trieline and mixtures thereof.

8. Process according to claim 1, wherein sodium hydroxide is used as an alkali hydroxide.

9. Process according to claim 1, wherein calcium or barium hydroxide is used as an earth-alkali hydroxide.

10. Process according to claim 1, wherein the N-chloroamide is reacted with a mixture of sodium and calcium hydroxide.

11. Process according to claim 1 wherein the reaction between the N-chloroamide and the alkali hydroxide, earth-alkali hydroxide or mixture thereof is effected at a temperature of between 0° and 100° C.

12. Process according to claim 11, wherein said reaction is effected at a temperature of between 0° and 80° C.

* * * * *